US00PP35088P2

(12) United States Plant Patent
van Noort

(10) Patent No.: US PP35,088 P2
(45) Date of Patent: Apr. 4, 2023

(54) ***COREOPSIS* PLANT NAMED 'MVNC1823'**

(50) Latin Name: *Coreopsis grandiflora*
Varietal Denomination: MVNC1823

(71) Applicant: Marco van Noort, Warmond (NL)

(72) Inventor: Marco van Noort, Warmond (NL)

(73) Assignee: MARCO VAN NOORT BREEDING BV, Warmond (NL)

( * ) Notice: Subject to any disclaimer, the term of this patent is extended or adjusted under 35 U.S.C. 154(b) by 0 days.

(21) Appl. No.: 17/948,404

(22) Filed: Sep. 20, 2022

(30) Foreign Application Priority Data

Feb. 8, 2022 (QZ) ..... PBR 2022/0408

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
See application file for complete search history.

*Primary Examiner* — Susan McCormick Ewoldt
(74) *Attorney, Agent, or Firm* — Penny J Aguirre

(57) ABSTRACT

A new cultivar of hybrid *Coreopsis* plant named 'MVNC1823' that is characterized by its neat, compact plant habit reaching an average of 50 cm in height and having stems of similar length, its long flowering period from late spring to early autumn in The Netherlands, its inflorescences with ray florets that are yellow in color with red centers, its inflorescences that are large in size, its resistance to powdery mildew, its high tolerance to heat and humidity, and its healthy foliage that maintains its bright green appearance.

2 Drawing Sheets

Botanical classification: *Coreopsis grandiflora*.
Variety denomination: 'MVNC1823'.

CROSS-REFERENCE TO RELATED APPLICATIONS

This application claims priority to European Community Plant Variety Office (CPVO) Plant Breeder's Rights Application No. 2022/0408 filed on Feb. 8, 2022, under 35 U.S.C. 119(f), the entire contents of which is incorporated by reference herein. This application is also co-pending with U.S. Plant Patent Applications filed for plants derived from the same breeding program that are entitled *Coreopsis* Plant Named 'MVNC1902' (U.S. Plant patent application Ser. No. 17/948,449), *Coreopsis* Plant Named 'MVNC1904' (U.S. Plant patent application Ser. No. 17/948,459), and *Coreopsis* Plant Named 'MVNC1906' (U.S. Plant patent application Ser. No. 17/948,477).

BACKGROUND OF THE INVENTION

The present invention relates to a new and distinct cultivar of *Coreopsis* plant, botanically known as *Coreopsis grandiflora*. 'MVNC1823' and will be referred to hereinafter by its cultivar name, 'MVNC1823'. The new cultivar of *Coreopsis* is an herbaceous perennial grown for landscape and container use.

The new cultivar arose from an ongoing breeding program conducted by the Inventor in Warmond, The Netherlands. The goal of the breeding program is to develop new cultivars of *Coreopsis grandiflora* that are early flowering and have dependable perennial habits, an abundance of flowers, healthy foliage with powdery mildew resistance combined with unique inflorescence coloration.

'MVNC1823' was selected by the Inventor as a seedling in a trial garden in Warmond, The Netherlands in July of 2017. The new cultivar arose from open pollination of unnamed (not patented) seedlings of *Coreopsis grandiflora* in the inventors breeding program. The seeds were pooled after collection and therefore the exact parents are unknown.

Asexual propagation of the new cultivar was first accomplished by stem cuttings in Lisse, The Netherlands in 2021 under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'MVNC1823' as a unique cultivar of *Coreopsis*.

1. 'MVNC1823' exhibits a neat, compact plant habit reaching an average of 50 cm in height and having stems of similar length.
2. 'MVNC1823' exhibits a long flowering period from late spring to early autumn in The Netherlands.
3. 'MVNC1823' exhibits inflorescences with ray florets that are yellow in color with red centers.
4. 'MVNC1823' exhibits inflorescences that are large in size.
5. 'MVNC1823' exhibits resistance to powdery mildew.
6. 'MVNC1823' exhibits a high tolerance to heat and humidity.
7. 'MVNC1823' exhibits healthy foliage that maintains its bright green appearance.

'MVNC1823' can be most closely compared to *Coreopsis grandiflora* cultivar 'Sonnenkind' (not patented) and cultivars derived from the same crosses; 'MVNC1902', 'MVNC1904', and 'MVNC1906'. 'Sonnenkind' is similar to 'MVNC1823' in having inflorescences with ray florets that are yellow in color with red centers. 'Sonnenkind' differs from 'MVNC1823' in having a lower resistance to powdery mildew, foliage that is not as healthy, and in producing fewer inflorescences. 'MVNC1902' differs from 'MVNC1823' in having inflorescences with ray florets that are bright red in color with yellow-orange margins. 'MVNC1904' differs from 'MVNC1823' in having inflorescences with ray florets that are cherry red in color with yellow margins. 'MVNC1906' differs from 'MVNC1823' in having inflorescences with ray florets that are lighter yellow in color with darker red centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Publications include listings on websites by Plantipp and Quality Cuttings.

BRIEF DESCRIPTION OF THE DRAWINGS

The accompanying color photographs illustrate the overall appearance and distinct characteristics of the new *Coreopsis*. The photographs were taken of a 1-year-old plant of 'MVNC1823' as grown outdoors in a 17 cm container in Warmond, The Netherlands.

The photograph in FIG. 1 provides a view of the plant habit of 'MVNC1823' in bloom.

Figure 1:
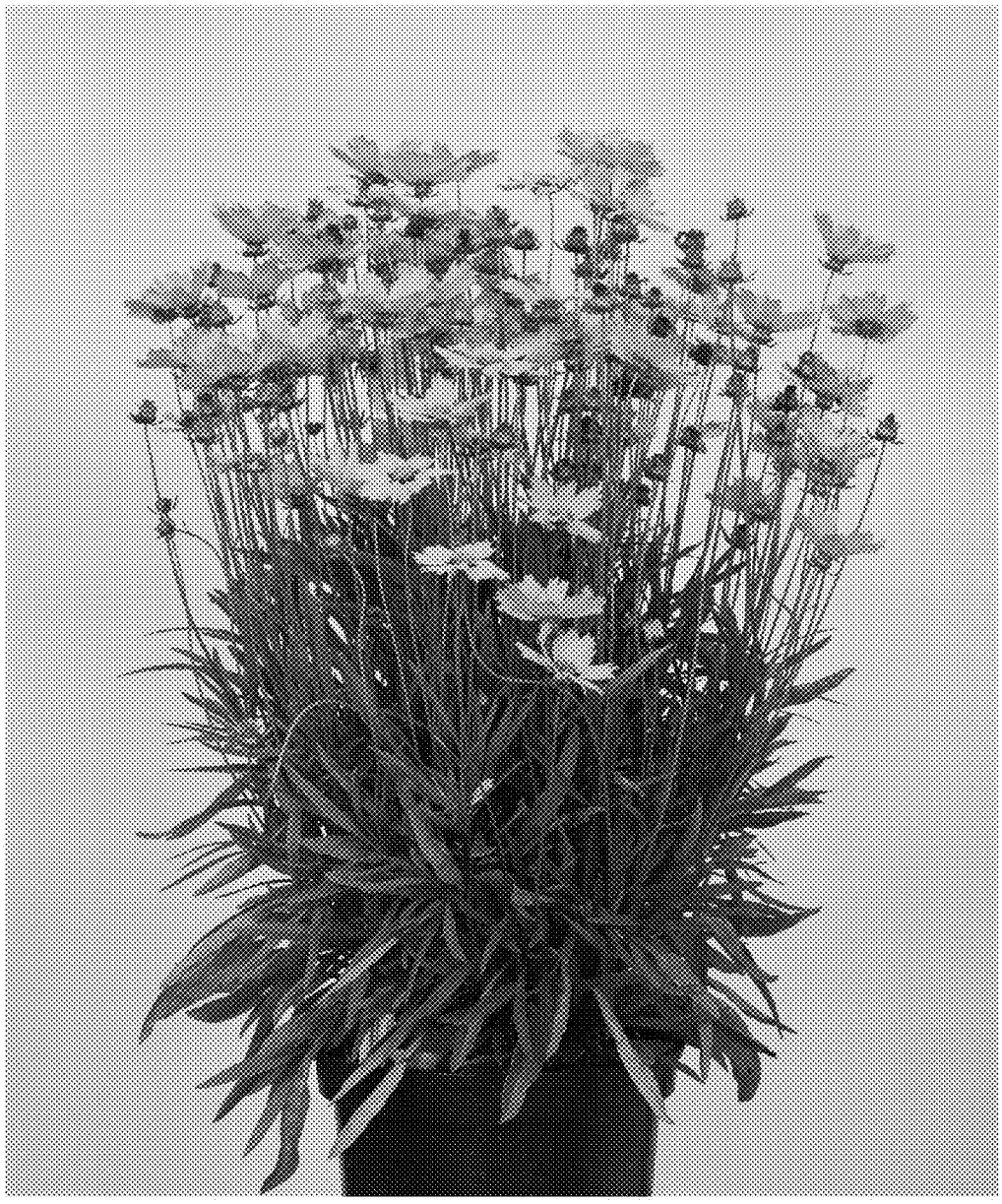
Figure 2:
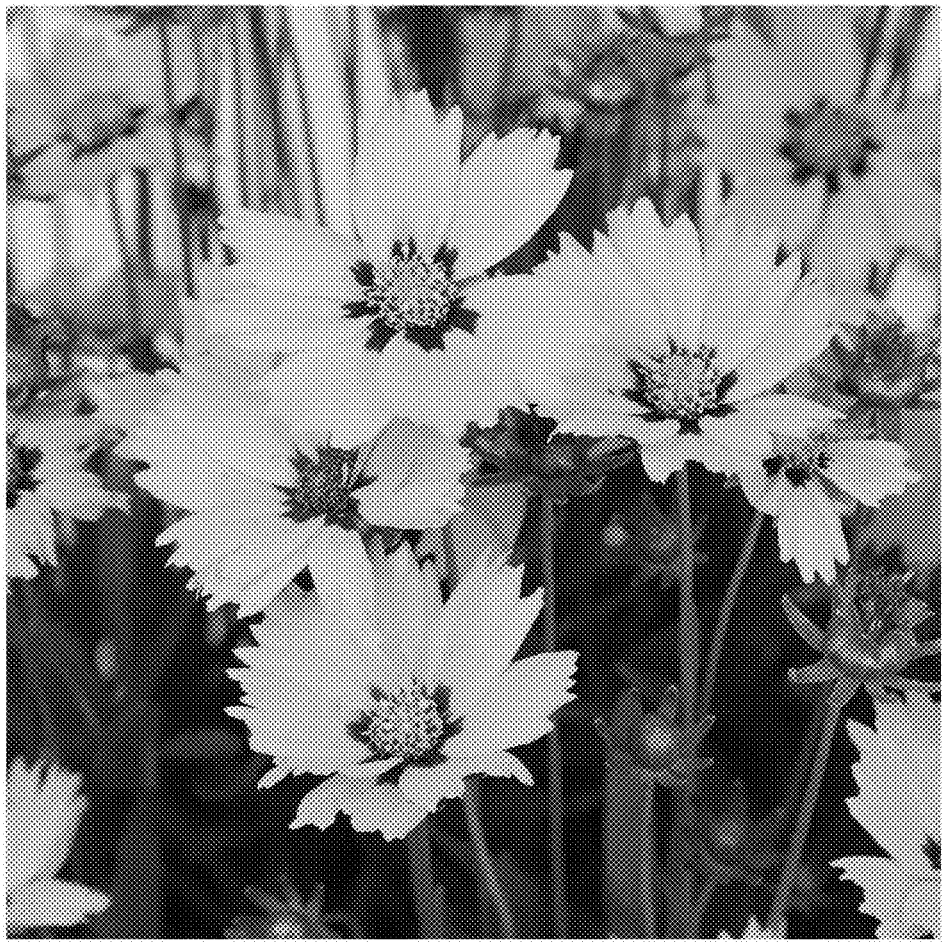

The photograph in FIG. 2 provides a close-up view of inflorescences of 'MVNC1823'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 1-year-old plants of 'MVNC1823' as grown outdoors in 17 cm containers in Warmond, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early late spring to early autumn in the Netherlands.

*Plant type*.—Herbaceous perennial.

*Plant habit*.—Clump-forming, bushy and compact, upright leafy flowering stems with inflorescences held above the foliage.

*Height and spread*.—Reaches an average of 50 cm in height and 43.8 cm in width and a one-year-old plant.

*Cold hardiness*.—At least to U.S.D.A Zone 4.

*Diseases and pests*.—Resistance to powdery mildew (*Podosphaera macularis*), no susceptibility or resistance to pests has been observed.

*Root description*.—Fibrous and fine, NN155A in color.

*Propagation*.—Stem cuttings.

*Root development*.—An average of 10 days for root initiation, an average of 20 weeks to produce a marketable plant.

*Growth rate*.—Moderate.

Branch description:

*Branch shape*.—Rounded, slightly axially ribbed.

*Branch color*.—146B, base between 146C and 152C.

*Branch size*.—Main and secondary stems; an average of 10.3 cm in length and 3 mm in width.

*Branch strength*.—Very strong.

*Branch surface*.—Glabrous.

*Branch aspect*.—Average of 10° to vertical.

*Branching quantity*.—An average of 44 main branches, 2 secondary branches per main stem.

*Internode length*.—An average of 5.4 cm.

Foliage description:

*Leaf division*.—Simple.

*Leaf margins*.—Entire.

*Leaf size*.—7.8 cm in length, 1.5 cm in width.

*Leaf shape*.—Lanceolate.

*Leaf base*.—Long attenuate to decurrent.

*Leaf apex*.—Acute.

*Leaf venation*.—Pinnate, color; upper surface NN137C, lower surface; 146A and 146B.

*Leaf attachment*.—Upper stem leaves nearly sessile, lower stem leaves petiolate.

*Leaf arrangement*.—Opposite.

*Leaf surface*.—Both surfaces very slightly glossy, smooth, glabrous and slightly leathery, margins are sparsely pubescent with short thin hairs; 0.2 mm in length, too small to measure color.

*Leaf color*.—Young upper surface 144A, young lower surface 146D, mature upper surface NN137C, mature lower surface 147B.

*Petioles*.—Lower stem leaves; average of 3.2 cm in length, 2 mm in diameter, v-shaped, surface smooth and glabrous, color; upper surface 146B, lower surface 144A, main vein 152B, margins sparsely pubescent with short thin hairs; an average of 1 mm in length and too small to measure color.

Flower description:

*Inflorescence type*.—Terminal capitulum consisting of ray florets and disc florets.

*Lastingness of inflorescence*.—Average of 10 days.

*Fragrance*.—Faint, pleasant.

*Quantity of inflorescences*.—1 per lateral stem, 130 per plant.

*Inflorescence size*.—1.5 cm in height, 5.1 cm in diameter, disc diameter 1.1 cm.

*Inflorescence buds*.—Globular in shape, an average of 9 mm in depth and 9 mm in diameter, dull surface; color; 152A to 152B, striped 153D.

*Peduncle*.—Rounded in shape, moderately strong, held in a vertical angle, an average of 18.1 cm in length and 1.5 mm in diameter, 144A in color, smooth, moderately glossy and glabrous surface.

Phyllaries (involucral bracts):

*Phyllary number.*—2 rows; total of 16, upper row 8, lower row 8.

*Phyllary size.*—Upper phyllaries; an average of 1 cm in length and 4 mm in width, lower phyllaries; an average of 1 cm in length and 2 mm in width.

*Phyllary color.*—Upper phyllaries upper surface; 152C, upper phyllaries lower surface; 144A, upper ⅔rd 152C, margins 154B, lower phyllaries upper surface; 137B, lower phyllaries lower surface; 137A.

*Phyllary texture.*—Upper phyllaries; smooth, glabrous, lower phyllaries; smooth, glabrous, slightly glossy.

*Phyllary apex.*—Acute.

*Phyllary base.*—Cuneate.

*Phyllary shape.*—Upper phyllaries; ovate, lower phyllaries; lanceolate to oblanceolate.

Ray florets:

*Number.*—8.

*Shape.*—Obovate, rotate.

*Size.*—An average of 2.7 cm in length and 1.6 cm in width.

*Apex.*—Cleft into 4 lobes.

*Base.*—Rounded to emarginate.

*Margins.*—Entire.

*Aspect.*—Flat, horizontal.

*Texture.*—Upper surface; matte, glabrous, velvety, lower surface; very slightly glossy, glabrous, non-velvety.

*Color.*—When opening upper surface; 14A to 14B, base between 46A and 187C, when opening lower surface; 14A to 14B, base 197D, when fully open upper surface; 14A, base between 46A and 187C, fully open lower surface; 14B, base 197D.

Disc florets (male and female):

*Number.*—An average of 100.

*Shape.*—Tubular.

*Base.*—Lower 85% fused.

*Size.*—About 9 mm in length and 2.5 mm in width.

*Apex.*—Acute.

*Surface.*—Glabrous, moderately glossy.

*Margins.*—Entire.

*Color.*—When opening upper and lower surface; 17A, mid-section, base 13C, fully open upper and lower surface; 15C, tips 15A, lower half 18D.

*Receptacle.*—Average of 1 mm in height, 3.5 mm in diameter, 146D in color.

*Receptacle spines.*—Linear, 100 per disc floret, soft, narrow acute apex, narrow cuneate base, surface is glabrous, moderately glossy, color; apex 16A, mid-section 3D, base 154D.

Reproductive organs:

*Gynoecium.*—1 Pistil; an average of 7 mm in length, style; 6.5 mm in length, 150D in color, stigma; unequal decurrent, 17B in color, ovary; 145C.

*Androecium.*—5 stamens, filament; 2.5 mm in length, 150D in color, anther; linear, 1.5 mm in length, 13C, base 197A, pollen; moderate in quantity and 17B in color.

*Seed.*—Seed development has not been observed.

It is claimed:

1. A new and distinct cultivar of *Coreopsis* plant named 'MVNC1823' as herein illustrated and described.

* * * * *